US009763631B2

(12) United States Patent
Hefetz et al.

(10) Patent No.: US 9,763,631 B2
(45) Date of Patent: Sep. 19, 2017

(54) SYSTEMS AND METHODS FOR IMAGING PLURAL AXIAL LOCATIONS

(71) Applicant: General Electric Company, Schenectady, NY (US)

(72) Inventors: Yaron Hefetz, Kubbutz Alonim (IL); Jonathan Sachs, Tirat Carmel (IL); Gil Kovalski, Tirat Carmel (IL); Avi Bar-Shalev, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 342 days.

(21) Appl. No.: 14/488,769

(22) Filed: Sep. 17, 2014

(65) Prior Publication Data

US 2016/0073975 A1    Mar. 17, 2016

(51) Int. Cl.
*A61B 5/05* (2006.01)
*A61B 6/03* (2006.01)
*A61B 6/04* (2006.01)
*A61B 6/00* (2006.01)

(52) U.S. Cl.
CPC .......... *A61B 6/037* (2013.01); *A61B 6/0407* (2013.01); *A61B 6/0457* (2013.01); *A61B 6/469* (2013.01); *A61B 6/5205* (2013.01)

(58) Field of Classification Search
CPC ..... A61B 6/037; A61B 6/5205; A61B 6/0457; A61B 6/0407; A61B 6/469
USPC ................................................. 600/407–436
See application file for complete search history.

(56) References Cited

U.S. PATENT DOCUMENTS

| | | |
|---|---|---|
| 6,140,650 A | 10/2000 | Berlad |
| 6,239,438 B1 | 5/2001 | Schubert |
| 6,748,044 B2 | 6/2004 | Sabol et al. |
| 6,943,355 B2 | 9/2005 | Shwartz et al. |
| 7,026,623 B2 | 4/2006 | Oaknin et al. |
| 7,381,959 B2 | 6/2008 | Manjeshwar et al. |
| 7,671,331 B2 | 3/2010 | Hefetz |
| 9,427,205 B1 * | 8/2016 | Chen ................... A61B 6/032 |
| 2002/0191828 A1 | 12/2002 | Colbeth et al. |
| 2005/0145797 A1 | 7/2005 | Oaknin et al. |
| 2006/0108532 A1 | 5/2006 | Ohana et al. |
| 2007/0018108 A1 | 1/2007 | Kitamura |

(Continued)

OTHER PUBLICATIONS

Meikle et al., "Accelerated EM reconstruction in total-body PET: potential for improving tumour detectability," 1994, Physics in Medicine and Biology, vol. 39, pp. 1689-1704.

(Continued)

*Primary Examiner* — Sanjay Cattungal
(74) *Attorney, Agent, or Firm* — Dean D. Small; The Small Patent Law Group, LLC

(57) ABSTRACT

An imaging system is provided including a gantry, a bed, nuclear medicine (NM) imaging detectors, and a processing unit. The NM imaging detectors are disposed about the bore of the gantry. The processing unit is operably coupled to the imaging detectors, and is configured to acquire first NM imaging information of the object with the imaging detectors in a first axial position, iteratively actuate the gantry in a series of steps between the first axial position and the second axial position, acquire additional NM imaging information of the object at each of the steps, and reconstruct an image of the object using the first NM imaging information and the additional NM imaging information.

20 Claims, 10 Drawing Sheets

(56) References Cited

U.S. PATENT DOCUMENTS

| | | | | |
|---|---|---|---|---|
| 2011/0110486 A1* | 5/2011 | Bouhnik | A61B 6/032 | |
| | | | | 378/8 |
| 2012/0070057 A1* | 3/2012 | Zhang | G06T 11/005 | |
| | | | | 382/131 |
| 2012/0278055 A1* | 11/2012 | Schweizer | A61B 6/037 | |
| | | | | 703/11 |
| 2013/0294570 A1* | 11/2013 | Hansis | A61B 6/5235 | |
| | | | | 378/4 |
| 2014/0003689 A1* | 1/2014 | Asma | G06T 11/006 | |
| | | | | 382/131 |
| 2016/0012615 A1* | 1/2016 | Gao | G06T 11/005 | |
| | | | | 382/131 |

OTHER PUBLICATIONS

Riddell et al., "Noise reduction in oncology FDG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-121.

Park et al., "Performance of a high-sensitivity dedicated cardiac SPECT scanner for striatal uptake quantification in the brain based on analysis of projection data," Med. Phys. 40 (4), Apr. 2013.

* cited by examiner

SYSTEMS AND METHODS FOR IMAGING PLURAL AXIAL LOCATIONS

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data, which may be used to generate a planar (2D) or a three-dimensional (3D) image of the subject.

NM imaging systems systems may have moving detector heads, such as gamma detectors positioned to focus on a region of interest. For example, a number of gamma detectors may be moved (e.g., rotated) to different angular and/or rotational positions for acquiring image data.

However, such detector heads may have a relatively small field of view along an axial direction, for example. Thus, to image larger portions of the body, or to image organs that do not completely fall within the field of view, it may be necessary to acquire a series of images at different times. However, for dynamic studies, images acquired at different times may not be as clinically useful as desired.

Other nuclear cameras, such as the General Electric Discovery NM 530c (http://www3.gehealthcare.com/en/products/categories/nuclear_medicine/cardiac_cameras/discovery_nm_530c), for example, may be based on multiple pinhole configurations, and may also have a limited axial Field Of View (FOV). For example, a nuclear camera that is optimized for cardiac imaging may have a limited FOV in all 3 dimensions, and may be capable of rapidly acquiring a 3D image of the limited-sized FOV. It may be noted that a multi-pinhole based camera may not require motion (e.g., rotation) of a gantry or support structure, and/or of detector units relative to each other, to acquire a single-photon emission computed tomography (SPECT) image. However, some of these cameras may perform a limited motion during SPECT acquisition to acquire data from more view-points with respect to the target tissue.

BRIEF DESCRIPTION OF THE INVENTION

In one embodiment, an imaging system is provided including a gantry having a bore therethrough, a bed, plural nuclear medicine (NM) imaging detectors, and a processing unit. The bed is translatable between a first axial position and a second axial position along an axis of the bore of the rotating gantry, and is configured to support an object to be imaged. The NM imaging detectors are disposed about the bore of the gantry. The NM imaging detectors define an axial field of view and an in-plane field of view. The processing unit is operably coupled to the imaging detectors, and is configured (e.g., programmed) to acquire first NM imaging information of the object from the imaging detectors with the imaging detectors in the first axial position; iteratively actuate the gantry in a series of steps between the first axial position and the second axial position; acquire additional NM imaging information of the object at each of the steps; and reconstruct an image of the object using the first NM imaging information and the additional NM imaging information, wherein the image corresponds to an axial field of view that is larger than the axial field of view of the imaging detectors.

In another embodiment, a method for imaging is provided. The method includes acquiring first nuclear medicine (NM) imaging information of an object to be imaged with plural NM imaging detectors at a first axial position. The imaging detectors are disposed about a gantry having a bore therethrough, with the object disposed on a bed translatable along an axis of the bore between the first axial position and a second axial position. The imaging detectors have an axial field of view. The method also includes iteratively actuating the gantry in a series of steps between the first axial position and the second axial position, as well as acquiring additional NM imaging information of the object at each of the steps. Further, the method includes reconstructing an image of the object using the first NM imaging information and the additional NM imaging information, wherein the image corresponds to an axial field of view that is larger than the axial field of view of the imaging detectors.

In another embodiment, an imaging system is provided that includes a first gantry having a bore therethrough, a second gantry axially aligned with the first gantry and configured to be translatable axially relative to the first gantry, a bed that is translatable along an axis of the bore of the first gantry, plural nuclear medicine (NM) imaging detectors disposed about the bore of the first gantry and the second gantry, the imaging detectors having an axial field of view; and a processing unit operably coupled to the imaging detectors. The processing unit is configured to axially translate the bed and the second gantry with respect to the first gantry to position the first gantry about a first region of interest and to position the second gantry about a second region of interest; acquire, concurrently, NM imaging information from the imaging detectors of the first region of interest and the second region of interest; and reconstruct an image using the NM imaging information.

DETAILED DESCRIPTION OF THE INVENTION

Figure 1:
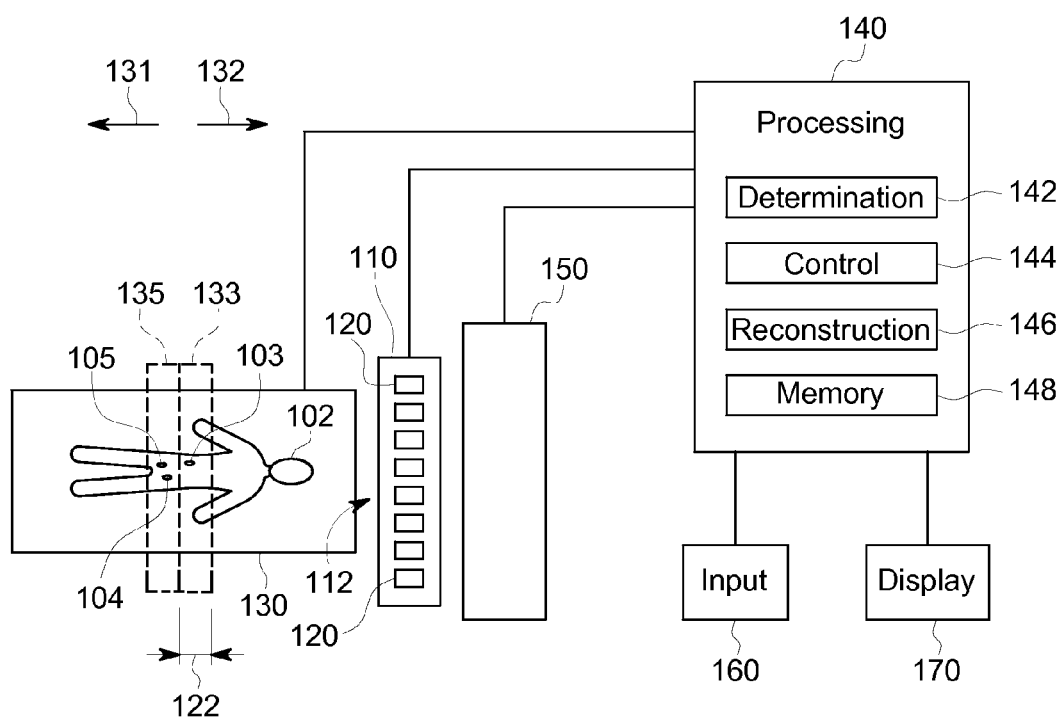
FIG. 1 is a schematic view of an imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for nuclear medicine (NM) imaging. Generally, a radiopharmaceutical may be introduced into an object to be imaged (e.g., via injection into a human or animal patient), and used for imaging, for example a portion of an object such as one or more organs of interest. NM imaging may be useful, for example, in conjunction with functional studies of one or more organs of interest. Various embodiments provide for dynamic imaging of a region of interest (ROI) that is larger than a field of view of one or more gamma cameras or other detectors used to acquire imaging information for the dynamic imaging. Dynamic imaging of a ROI larger than the field of view of the camera(s) or detector(s) may be useful, for example, for dynamic renal studies, for which both the kidneys and bladder are to be imaged, or, as another example, for patients whose kidneys are not at the same relative height in the pelvis (for example, due to a kidney transplant). As one more example, dynamic studies of the lungs or other organs may require imaging of a ROI that is larger than a field of view of a camera or detector.

In various embodiments, during performance of a single imaging scan (e.g., collection or acquisition of information processed as a group to provide one or more images, in contrast to a series of different imaging scans for which information is not processed as a group), a bed supporting an object to be imaged may be repeatedly or iteratively moved between at least two axial positions, thereby providing imaging information over a greater range than an axial field of view (FOV) of detectors of a system. For example, a camera (or cameras) may be used to sequentially image two axial FOV's for a dynamic scan of two (or more) organs that are located too far apart to be covered by the axial FOV of the camera, or, as another example, for a dynamic scan of a region of interest that is larger than the axial FOV of the camera. In some embodiments, a bed supporting a patient for a dynamic renal study may be translated back and forth during the study to intermittently collect imaging information of the kidneys and bladder (in contrast to collecting all imagining information for use for the kidneys over a first duration and all imaging information for use with the bladder over a second duration that does not overlap with the first duration).

The back and forth motion of the bed may be generally continuous in some embodiments, and may be performed as a series of discrete steps in other embodiments. Further, it may be noted that the FOV's or corresponding axial positions may be contiguous, separated, or overlap in various embodiments. Further still, more than two FOV's or ranges may be employed, with the FOV's or ranges contiguous, separate (or discrete), or a combination of contiguous and separate (e.g., some ranges contiguous and some ranges discrete). In some embodiments, the ranges may be covered in a cyclic fashion, with the duration of each cycle (or time spent at a given axial position before starting a new cycle at a different axial position) being shorter than a time required for or corresponding to a dynamic process being studied (e.g., time required for upload and/or washout). Further, in various embodiments, one or more images may be corrected or adjusted to account for isotope lifetime.

In some embodiments, instead of using only a single gantry (or ring upon which detectors are positioned), two or more gantries or detector rings may be used in tandem. For example, if each gantry or ring has an axial FOV of about 20 centimeters, two gantries or rings used in tandem may provide an axial FOV of about 40 centimeters. Further, at least one of the gantries or rings may be axially adjustable with respect to another gantry or ring to provide for simultaneous or concurrent imaging in two different axial positions. Instead of cycling back and forth between two FOV's, imaging information for both FOV's may be acquired at the same time. Optionally, each gantry or ring may have columns, with each column having a smaller FOV than the entire gantry or ring.

Various scanning strategies (e.g., strategies for moving detectors rotationally about a gantry and axially along a bore of the gantry relative to an object being imaged) may be employed for overlapping FOVs, adjacent or contiguous FOVs (or FOVs sharing a common border), or non-contiguous FOVs (or FOVs spaced apart or not sharing a common border or overlapping). For example, for overlapping FOVs, if two or more organs of interest (or ROIs) are close enough that the two or more organs of interest may be viewed without shifting a camera the width of one full FOV, the bed supporting a patient may be axially translated back and forth less than a full FOV. For example, the bed may be axially translated only enough so that the entire region of interest is covered.

As another example, for non-contiguous FOVs, if two or more organs of interest (or ROIs) are situated far enough apart such that the two or more organs may not be seen by shifting a camera view the width of one full FOV or less, the bed may be axially translated between two separate FOVs, with an intermediate zone between the FOVs not imaged.

In some embodiments, the bed may be axially translated in a sinusoidal or otherwise periodic and generally continuous fashion. A bed may be understood as being axially translated in a generally continuous fashion when the motion between two endpoints of travel is continuous. For example, the bed may pause momentarily at an endpoint to transition from motion in one direction to motion in an opposite direction while still being translated generally continuously as used herein. In some embodiments, during acquisition of imaging information (e.g., during all or a portion of an acquisition period), the bed may be translated back and forth in an undulating or oscillating motion. By using a generally continuous motion, the acceleration or jarring associated with stopping and starting of the bed at numerous axial steps may be reduced, thereby reducing patient motion and discomfort.

It may be noted that, while 3-dimensional imaging (e.g., single photon computed tomography (SPECT)) may provide more detailed or complete images than planar imaging, planar imaging may provide sufficient enough image quality for use in dynamic studies. Accordingly, planar imaging may be utilized in various embodiments. For example, a sequence of actuations performed during acquisition of imaging information as part of a scan may be as follows: First, with the bed being translated in a first direction axially through the bore, imaging information is acquired with the detectors stationary at a single rotational position. Then, when the bed reaches the end of travel in the first direction, and is reversing course to travel in a second direction opposite of the first direction, the detectors may be rotated (e.g., rotated such that the detectors move the width of a detector head or detector field of view) to a new rotational position. The bed may then be translated in the second direction axially through the bore, with imaging information acquired with the detectors until the time when the bed reaches the end of travel in the second direction. While the bed switches directions, the detectors may again be rotated (e.g., rotated such that the detectors once again move the width of a detector head or a detector field of view). The back and forth motion of the bed along with the rotation at the end positions of the bed may be repeated until a desired amount of imaging information has been acquired.

In various embodiments, focused imaging may be used to enhance dynamic imaging. For example, a dynamic portion of a study may be performed using planar imaging (e.g., detector heads not rotating with respect to each other) to save acquisition time during a dynamic portion of a study. Further, attenuation correction may be applied using SPECT information acquired before or after the dynamic portion, or using CT information acquired before or after the dynamic portion (for example, to help distinguish the organ of interest from interfering tissue). As another example, a lower dose or different type of isotope may be used for locating a target organ (or organs) of interest before a dynamic acquisition.

In some embodiments, stationary detectors may be aimed at an organ (or organs of interest). The resulting image may be of relatively low quality due to a relatively low number of views, but may be corrected with subsequently acquired SPECT information (e.g., information acquired with a larger number of views per detector). For example, a first pass (or group of passes) may be performed with stationary or non-pivoting detectors (it may be noted that a "stationary" detector may rotate with a gantry), and then imaging in a second pass (or group of passes) using SPECT over a region of interest. In some embodiments, a later pass (or group of passes) may be taken over an entire transaxial volume including the region of interest.

In some embodiments, detectors may be focused on a target organ (or organs) during a fast changing part of an acquisition, and used to image the remainder of a FOV during slowly varying times. Further, a greater percentage of imaging time may be spent with detectors focused on a target organ (or organs) than on non-target portions of one or more FOV's.

In various embodiments, a panoramic image may be created from each sweep or rotation of a detector head. Such an image may provide a somewhat distorted version of a frame acquired using a parallel hole collimator. However, the information may still be useful. For example, the panoramic image may be displayed with a corresponding forward projection image (e.g., an image derived using CT information acquired using a similar procedure as the emission or NM projections)). Further, an additional forward projection of CT information at an "undistorted" view may be provided, for example a projection of CT information corresponding to a view angle at the middle or center of the sweep of the detector head.

Various embodiments may be employed with different imaging protocols. For example, in connection with multi-gating imaging (MUGA), some parts of a fast changing organ may be imaged using planar imaging, and/or with stationary or non-pivoting detectors. As another example, a first pass of a cardiac imaging protocol may be performed stationary or non-pivoting detectors, with subsequent SPECT imaging. As one more example, in a renal imaging protocol for imaging the kidneys and bladder may be axially displaced from each other. The axial position of a patient with a bed may be controlled to alternate between two or more FOV's for interleaved or intermittent imaging of the axially displaced ROI's. Further example protocols that may be performed using one or more aspects of embodiments disclosed herein include gastrointestinal bleeding studies, gall bladder ejection fraction studies, and dynamic bone studies.

It may be noted that, while in some embodiments detectors may rotate with a gantry and/or with respect to each other, in other embodiments detectors may not rotate about a patient. For example, in some embodiments, an imaging system is provided that includes a plurality of detector units, each fitted with a pinhole detector. The camera of such an imaging system may be configured to acquire a 3D image of a FOV smaller than an entire Region Of Interest (ROI). Additionally or alternatively, the ROI may be composed of several sub-ROIs that are not contiguous, such as two or more distinct organs (e.g., 2 kidneys, or 1 or 2 kidneys and a bladder). While each sub-ROI may be smaller than the FOV, the totality of the ROI still may not fit within the FOV of the camera due to positioning or separation of the sub-ROIs.

In various embodiments, to acquire a dynamic (4D) image of the ROI with a camera having a FOV smaller than the ROI, the FOV of the camera may be repeatedly moved in respect to the patient body (for example, by moving the camera with respect to the patient, or, as another example, by moving the patient with respect to the camera) such that two or more portions of the ROI are scanned several times during the entire acquisition. It may be noted that motion of the FOV of the camera with respect to the patient body may be in an axial direction, a transaxial direction, a depth direction, or combination of two or more of axial, transaxial, or depth directions.

It may be noted that each sub-ROI may be imaged successively at time intervals corresponding to the time during which an image is expected to noticeably, significantly, or substantially change due to the dynamic of a particular isotope with respect to an organ or organs of interest. For example, each sub-ROI may be successively imaged at time intervals shorter than the expected time in which the image is expected to substantially change due to the dynamic of the radioisotope on the organ (or organs) in that sub-ROI. It may be noted that the time intervals may vary according to the type of organ, a medical condition (e.g., type of disease), and/or other patient characteristics (e.g., age, weight, or gender, among others). Additionally, the time intervals may vary during the acquisition due to the nature of the dynamic evolution of the radioisotope within the patient. For example, the changes in the distribution of the radioisotope in the body is often relatively rapid immediately or shortly after the injection of the radioisotope into the body, while the rate of changes in the distribution of the radioisotope in the body later is relatively slower. Thus, in some embodiments, the time intervals between sub-ROIs may be relatively shorter at the beginning of the acquisition and may be relatively longer at later stages.

In some embodiments, each time interval in which a sub-ROI is visited is long enough to acquire data sufficient to form a medically meaningful, or diagnostically useful, image of the sub-ROI. In such cases, each "visit" of a sub-ROI may be reconstructed independently. However, in some embodiments, each visit to a sub-ROI may be too short to acquire a large enough data set for a medically meaningful, or diagnostically useful, image of the sub-ROI, and reconstruction of the sub-ROI may be performed using information acquired during plural visits to the sub-ROI. Generally, the time required to acquire a medically meaningful (e.g., with low enough noise) SPECT image of a sub-ROI is longer than the time it takes acquire a medically meaningful planar image of the same sub-ROI. Accordingly, in some embodiments, planar images of the sub-ROIs may be obtained. Alternatively, a synthetic planar image may be created (using methods known in the art) from SPECT images. A dynamic image created from these synthetic planar images may be more familiar to a radiologist or other practitioner reading the image. Additionally, synthetic planar images may have less noise than the corresponding slices of original SPECT images.

In various embodiments, a dynamic 3D (SPECT) distribution vs. time, or a dynamic 2D (planar) distribution vs. time may be created from an acquired data set. To form a dynamic image, missing data of one or more sub-ROIs may be interpolated for the times in which each sub-ROI was not imaged (e.g., the times at which one or more other sub-ROIs were imaged). In some embodiments, interpolation may be achieved by modeling the dynamics of the image in a sub-ROI over the time of interest from several imaging information datasets that were acquired at corresponding different times. Further, in some embodiments, isotope half-life may be compensated for. Further still, other known or measured effects (e.g., the behavior of the distribution in non-target (or background) tissue) may be compensated for.

In various embodiments, data utilized for background subtraction may be acquired later in the acquisition, or even after the dynamic acquisition has ended, and the distribution of radioisotope is stable or slowly changing. Such measurements may include imaging of non-target tissue or out-of-ROI tissue, and may be used for removing image artifacts as known in the art.

A technical effect provided by various embodiments includes improved imaging, for example improved NM imaging for dynamic studies. A technical effect of various embodiments includes allowing performance of dynamic imaging of one or more ROI's that are larger than an axial field of view of a camera. A technical effect of various embodiments includes providing simultaneous, concurrent, or temporally interleaved acquisition of NM imaging information for two or more FOV's.

FIG. 1 provides a schematic view of an imaging system 100 formed in accordance with various embodiments. The depicted imaging system 100 includes a gantry 110, nuclear medicine (NM) imaging detectors 120 disposed about the gantry 110, a bed 130, a processing unit 140, a computed tomography (CT) acquisition unit 150, an input unit 160, and a display unit 170. The processing unit 140 in the illustrated embodiment is configured to control the various components to acquire imaging information and to reconstruct one or more images. For example, the processing unit 140 may control the bed 130 and gantry 110 to acquire imaging information for a dynamic study of a ROI having an axial FOV larger than the axial FOV of the detectors 120.

In the illustrated embodiment, a patient 102 is disposed on the bed 130 for performance of a dynamic renal study. The patient 102 has a first kidney 103, a second kidney 104, and a bladder 105. As seen in FIG. 1, the first kidney 103 and second kidney 104 are located at different heights relative to the pelvis of the patient 102, for example due to one of the kidneys being transplanted. Further, as seen in FIG. 1, the detectors 120 of the gantry 110 define an axial FOV having a width 122. As shown in FIG. 1, the width 122 of the axial FOV of the detectors 120 is not sufficient to cover the first kidney 103, second kidney 104, and bladder 105 at the same time. For example, the width 122 may be about 20 centimeters. Accordingly, to dynamically image the first kidney 103, second kidney 104, and bladder 105, the bed 130 may first be actuated along the axis of the bore 112 in a first direction 132 until the first kidney 103 is within the FOV of the detectors 120 at a first axial position 133 (in the first axial position 133, the gantry 110 and detectors 120 are positioned about the first kidney 103). The bed 130 may then be actuated further in the first direction 132 until the second kidney 104 and the bladder 105 are within the FOV of the detectors 120 at a second axial position 135 to collect imaging information for the second kidney 104 and bladder 105 (at the second axial position 135, the gantry 110 and detectors 120 are positioned about the second kidney 104 and bladder 105). Then the bed 130 may be moved back and forth along first direction 132 and second direction 131 (either generally continuously or in a series of steps) to acquire imaging information of the two FOV's in a temporally interleaved fashion, with the detectors 120 rotated about the gantry 110 during different points of the cycling back and forth to provide a variety of views for each detector 120. It may be noted that, in some embodiments, the detectors may be configured as a multiple-pinhole based camera or other configuration that need not necessarily rotate during an imaging process (e.g., the gantry or other support structure may not rotate during imaging, with only the bed articulated along an axial direction during acquisition of imaging information).

The depicted input unit 160 is configured to obtain input corresponding to a scan to be performed, with the processing unit 140 using the input to determine one or more scan settings (e.g., distance(s) for axial translation between steps, angular ranges for rotational steps, length or duration of imaging steps, length or duration of entire imaging process, or the like). The input unit 160 may include a keyboard, mouse, touchscreen or the like to receive input from an operator, and/or may include a port or other connectivity device to receive input from a computer or other source. The display unit 170 is configured to provide information to the user. The display unit 170 may be configured to display, for example, one or more images reconstructed by the processing unit 140 (e.g., images for dynamic studies). The images may be displayed at or near a time of acquisition and/or may be displayed or stored for display at a later time. The display unit 170 may include one or more of a screen, a touchscreen, a printer, or the like.

The depicted gantry 110 is configured as a rotating gantry. The gantry 110 rotates about the bore 112. The detectors 120 are attached to the gantry 110, and rotate with the gantry 110, so that rotation of the gantry 110 provides different rotational positions for the detectors 120 to provide different views from the detectors 120. Imaging information of an object or portion thereof disposed within the bore of the gantry 110 may be collected, detected, or acquired by the detectors 120.

Figure 2:
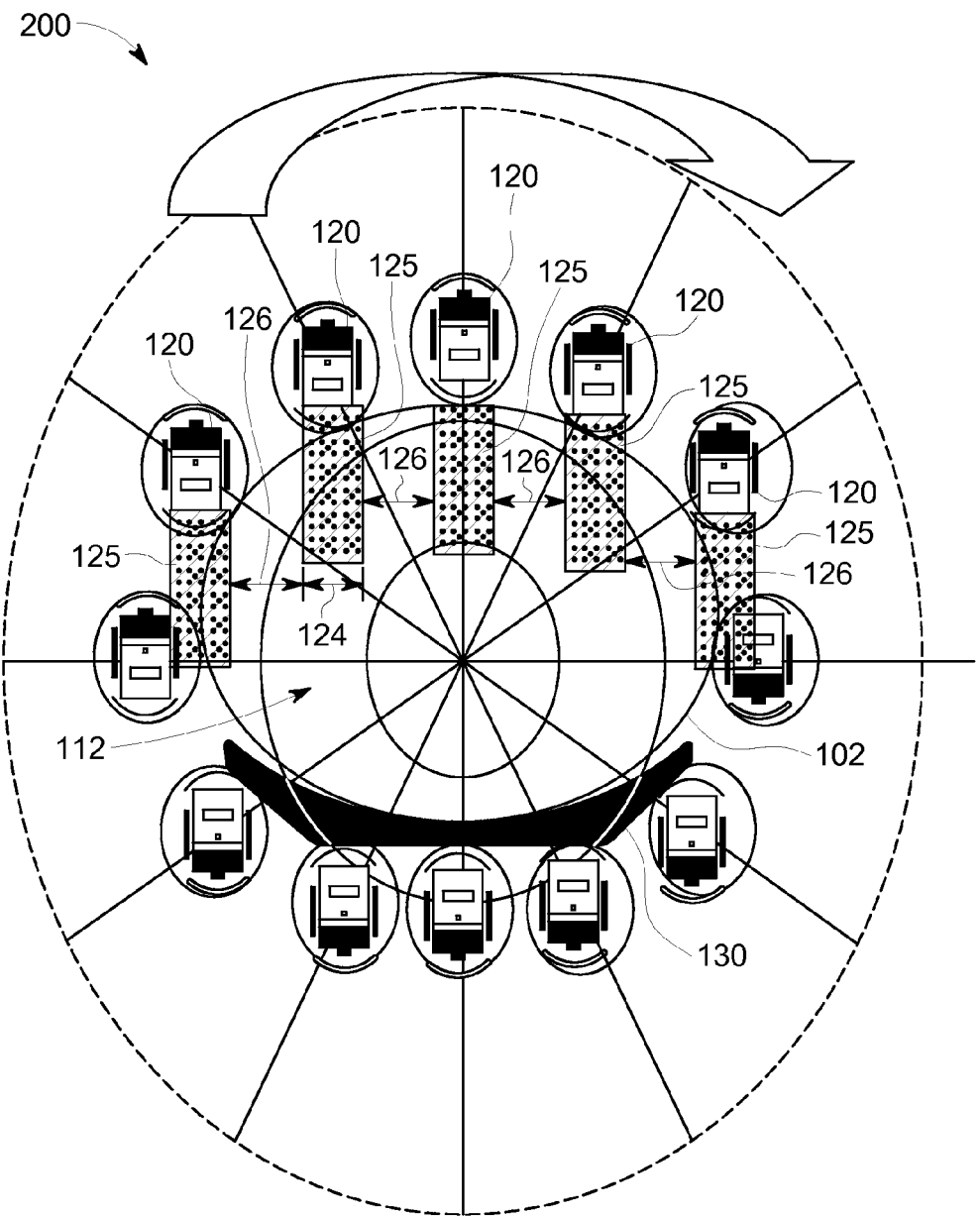
FIG. 2 is a schematic view of the gantry and detectors of the imaging system of FIG. 1 at a first rotational position.

The detectors 120 are positioned about the gantry 110 and are configured to rotate with the gantry 110. For example, as seen in FIG. 2, the detectors 120 are disposed about the bore 112 of the gantry 110. The detectors 120 have an axial FOV (e.g., shown as having width 122 in FIG. 1) as well as an in-plane field of view 125 shown in FIG. 2. The width of the in-plane field of view 125 may be understood as extending across a portion of a plane that is transverse to an axis passing through the bore 112 of the gantry 110. The in-plane field of view thus may be understood as extending in a direction transverse and/or perpendicular to the direction in which the axial field of view extends. In the illustrated embodiment, the in-plane field of view 125 generally corresponds to the width of the detector head. For example, the detectors 120 may include parallel-hole collimators associated therewith. As seen in FIG. 1, with the detectors 120 disposed about the upper half of the bore 112 (e.g., above the bed 130 and patient 102) being used to acquire imaging information, a gap 126 is defined between adjacent detectors 120. Due to the gap 126 and the generally vertical orientation of the in-plane FOV 125 of each detector, the in-plane field of view 125 of each detector 120 does not overlap with the in-plane FOV of immediately adjacent detectors 120. To collect imaging information over the gaps 126, the detectors 120 may be rotated about the bore and used to collect imaging information in a series of steps until all portions of the gaps 126 have been covered. (For additional details regarding rotation of detectors in steps, see discussion below regarding FIGS. 2-4.)

Each detector 120 may include a detection surface constructed from detector tiles. The detector tiles may be CZT wafer detectors having pixels or anodes. The pixels may be sized and positioned the same as holes of an associated parallel-hole collimator and may be registered with the holes in some embodiments, or have different numbers or positions than the holes in other embodiments.

Further, each detector 120 may be configured as a detector head assembly, for example, a rotating head detector assembly. Thus, the detectors 120 may rotate or pivot with respect to each other and the gantry 110, in addition to rotating about the bore 112 with the gantry 110. For example, the detectors 120 may be maintained in aligned (e.g., all detectors substantially vertical as shown in FIG. 2) fashion with each other to acquire planar imaging information, and rotated or pivoted with respect to each other to acquire SPECT information. The rotating head detector assembly may be pivotally attached to a telescoping arm (not shown in FIG. 1 or 2). The detector head assembly may also include one or more analog front ends (AFE), as well as a digital readout board (DRB).

Returning to FIG. 1, the bed 130 is configured to support the patient 102 during imaging and also to move the patient 102 axially during imaging to position a desired portion of the patient 102 within the bore 112 of the gantry 110. The bed 130 may be translated using an actuation mechanism such as a motor coupled to a rack and pinion, or as another example, a cylinder. For example, in the illustrated embodiment, the bed 130 is configured to be translated between the first axial position 133 (at which the first kidney 103 is within the axial FOV of the detectors but the second kidney 104 and bladder 105 are not) and the second axial position 135 (at which the second kidney 104 and bladder 105 are within the axial FOV of the detectors but the first kidney 103 is not). The bed 130 in various embodiments may also be positioned at intermediate positions between the first and second axial positions during imaging. The bed 130 may be moved in a series of steps between the first and second axial positions, or may be moved continuously between the first and second axial positions during imaging.

The depicted processing unit 140 is operably coupled to the gantry 110, the detectors 120, the bed 130, the CT acquisition unit 150, the input unit 160, and the display unit 170. The processing unit 140, for example, may receive information from the input unit 160 describing or corresponding to a procedure or study to be performed on one or more organs of interest. The processing unit 140 may then determine which organs to locate for scanning, and control the CT acquisition unit 150 to perform a scout scan on the patient 102. Based on the scout scan, the processing unit 140 may determine the location of the organ or organs to be imaged, and select axial positions for the bed 130 relative to the gantry 110 for acquiring imaging information. The processing unit may then control the gantry to rotate the detectors 120 and translate the bed 130 pursuant to an imaging strategy for covering a FOV larger than an axial FOV of the detectors 120. Using information from the detectors 120, the processing unit 140 may then reconstruct an image and display the image via the display unit 170. The processing unit 140 may include processing circuitry configured to perform one or more tasks, functions, or steps discussed herein. It may be noted that "processing unit" as used herein is not intended to necessarily be limited to a single processor or computer. For example, the processing unit 140 may include multiple processors and/or computers, which may be integrated in a common housing or unit, or which may distributed among various units or housings.

As seen in FIG. 1, in the illustrated embodiment, the processing unit 140 includes a determination module 142, a control module 144, a reconstruction module 146, and a memory 148. Generally, the determination module 142 may determine the axial and rotational positions to be used in acquiring NM imaging information (e.g., based on protocol or procedure information from the display unit 170, and/or information from a scout scan, among others), as well as the steps to be used between the various axial and rotational positions). The control module 144, for example, may formulate and provide control signals to implement the acquisition steps determined by the determination module 142 (e.g., rotate the gantry 110, axially translate the bed 130, control the detectors 120 to acquire NM information). The reconstruction module 146 receives acquired NM imaging information from the detectors 120 and provides a viewable or otherwise usable image or images to a practitioner. It may be noted that the particular units or modules shown in FIG. 1 are meant by way of example, and that other arrangements of units or sub-units of the processing unit 140 may be employed in various embodiments. Further, other types, numbers, or combinations of modules may be employed in alternate embodiments, and/or various aspects of modules described herein may be utilized in connection with different modules additionally or alternatively. Generally, the various aspects of the processing unit 140 act individually or cooperatively with other aspects to perform one or more aspects of the methods, steps, or processes discussed herein.

In various embodiments, the depicted processing unit 140 is configured to acquire first NM imaging information of an object to be imaged (e.g., patient 102) with the detectors 120 at a first rotational position (e.g., rotational position 200 shown in FIG. 2) and a first axial position (e.g., axial position 133 shown in FIG. 1). The processing unit 140 of the illustrated embodiment is also configured to iteratively actuate the gantry 110 in a series of steps between the first rotational position (e.g., rotational position 200 shown in FIG. 2) and a second rotational position (e.g., one or more additional rotational positions configured to provide imaging information for areas corresponding to the gaps 126 between in-plane FOV's 125 of the detectors 120), as well as between the first axial position (e.g., axial position 133) and a second axial position (e.g., axial position 135). It may be noted that, as used herein, actuation of a component relative to the gantry may be understood as an actuation of the gantry. During the iterative actuation of the gantry 110, the processing unit 140 may acquire additional NM information (e.g., via detectors 120) of the object at each iterative step. Further, the depicted processing unit 140 is configured to reconstruct an image of the object using the first NM imaging information and the additional NM imaging information. With the detectors 120 positioned over two or more axial FOV's at different times during a single imaging information acquisition process (e.g., a process corresponding to a time of interest for a dynamic study), the reconstructed image has or corresponds to an axial FOV that is larger than the axial FOV (e.g., width 122) of the detectors 120. It may be noted that the "image" need not necessarily be limited to a single printed or otherwise displayed page or screen. The image for example, may be dynamically presented to a viewer (e.g., via display unit 170) during the acquisition process. The information used to reconstruct or present the image may be understood as being collected during a single, generally continuous acquisition or scanning process.

It may be noted that actuation of the gantry 110 as used herein need not necessarily involve movement of the gantry 110, but may also include movement of an object or component relative to the gantry 110. For example, to actuate the gantry 110 between the first and second axial positions, the bed 130 may be axially translated relative to the gantry 110. As used herein, iteratively actuating the gantry 110 between axial positions and rotational positions requires actuating the gantry 110 (e.g., via motion of the bed 130) back and forth between axial position as well as among rotational positions (e.g., via rotation of the gantry) multiple times for a single imaging or scanning process (e.g., dynamic study).

Thus, for example, imaging information for a first axial FOV (e.g., corresponding to kidneys) may be acquired at times t1, t3, t5, and t7, and imaging information for a second axial FOV (e.g., corresponding to the bladder) may be acquired at times t2, t4, t6, and t8. Thus, over a duration of an imaging time extending from time t1 to time t8, imaging information is collected alternately for the first and second axial FOV's, such that the imaging information may be understood as being acquired in a temporally interleaved fashion. Thus, the times of acquisition for each FOV overlap with each other. By collecting imaging information in a temporally interleaved fashion, imaging information for both axial FOV's may be acquired over the same time period or duration for dynamic studies, instead of collecting all information for one FOV at a first time and all information for a second FOV at a second, discrete, non-overlapping time. For the purposes of clarity and avoidance of doubt, translating a detector along a single helical path in a given orientation is not iteratively actuating the gantry 110 as used herein. As another example, for the purposes of clarity and the avoidance of doubt, merely collecting a group of imaging information at a first axial FOV, and subsequently collecting a group of imaging information at a second axial FOV, without collecting information for both FOV's in a temporally interleaved fashion, is not iteratively actuating the gantry 110 as used herein.

The processing unit 140 may also be configured to determine the size and/or number of steps (rotational and/or axial) to be employed as part of the iterative actuation. For example, one or more organs of interest may be identified from information acquired using SPECT (e.g., using the detectors 120) and/or using CT (e.g., via a scout scan performed using the CT acquisition unit 150). The processing unit 140 may then determine an overall area to be scanned, as well as the relative spacing of any organs to determine if overlapping, adjacent, or spaced apart FOV's are to be used. As another example, the size or angular displacement of rotational steps may be selected so that, for each detector, a subsequent FOV (e.g., the in-plane FOV for the next step) overlaps or borders the FOV of the preceding position. With the size of the rotational steps determined, the number of rotational steps may be determined so that the entire gap between each pair of adjacent detectors is covered.

An example of rotational steps for planar imaging (e.g., with the detectors maintained in an aligned fashion among the various rotational steps) will now be discussed with particular reference to FIGS. 2-4. Detectors 120 disposed about the bore 112 of a gantry are shown in a first rotational position 200 in FIG. 2. Each active detector 120 has an in-plane field of view 125 as seen in FIG. 2, with in-plane field of view 125 being generally vertically oriented and having a width 124. For the example discussed in connection with FIGS. 2-4, the detectors 120 are maintained in a generally vertical orientation for collection of planar imaging. For SPECT imaging, the detectors 120 could be pivoted or swept (e.g., pivoted in one or more directions to angular orientations at an angle to the vertical orientation shown in FIG. 2) while at each of the rotational positions of the gantry. Gaps 126 are present between in-plane FOV's 125 of adjacent detectors 120. Generally, the larger the patient or object to be imaged, the farther outward radially the detectors 120 will be positioned, and the larger the gaps 126 will be. Thus, additional rotational steps may be required for a larger patient than for a smaller patient.

Figure 3:
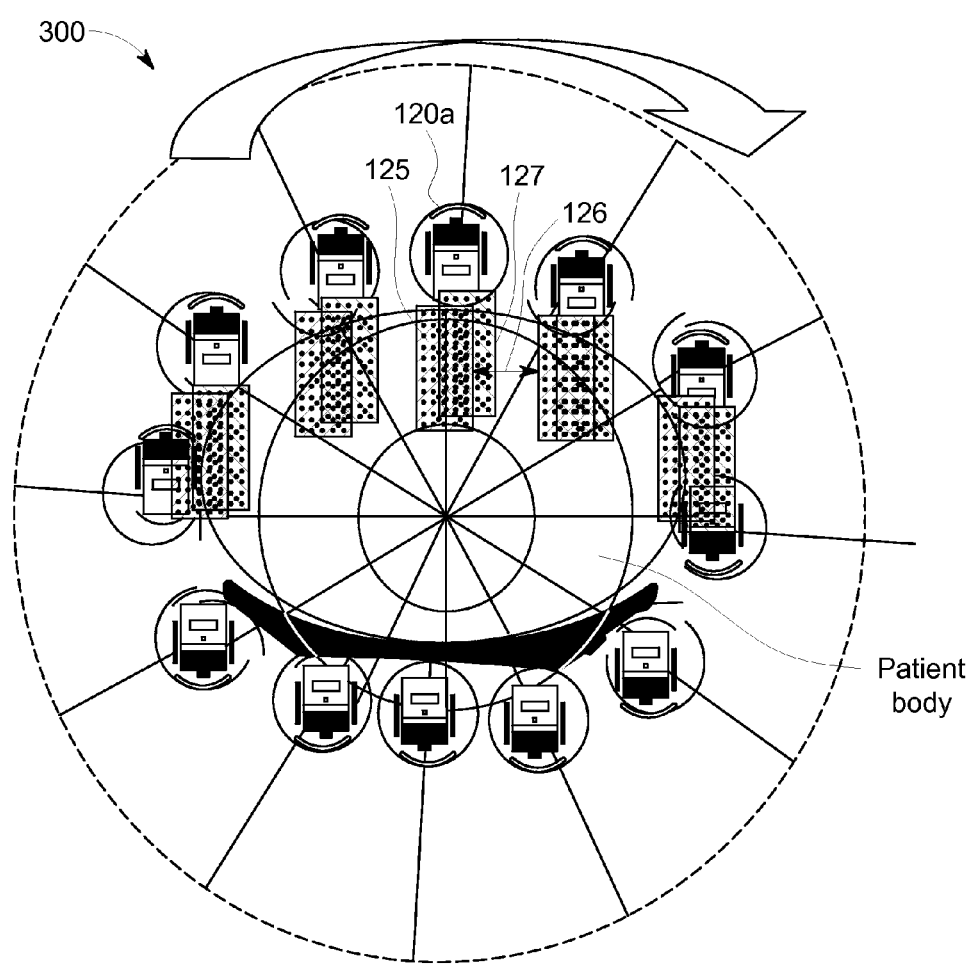
FIG. 3 is a schematic view of the gantry and detectors of the imaging system of FIG. 1 at a second rotational position.

FIG. 3 illustrates the detectors 120 at a second rotational position 300. The detectors 120 have been rotated clockwise relative to the first rotational position 200 shown in FIG. 2. For the detector 120a, for example, the in-plane FOV 127 at the second rotational position 300 is disposed generally to the right of (but still overlapping at least slightly) the in-plane FOV 125 corresponding to the first rotational position 200. Thus, additional imaging information may be acquired corresponding to the FOV 127 to supply information for some, but not all, of the gap 126. Because portions of the gap 126 are not covered by either the FOV 125 or the FOV 127, a subsequent third step may be employed for complete coverage.

Figure 4:
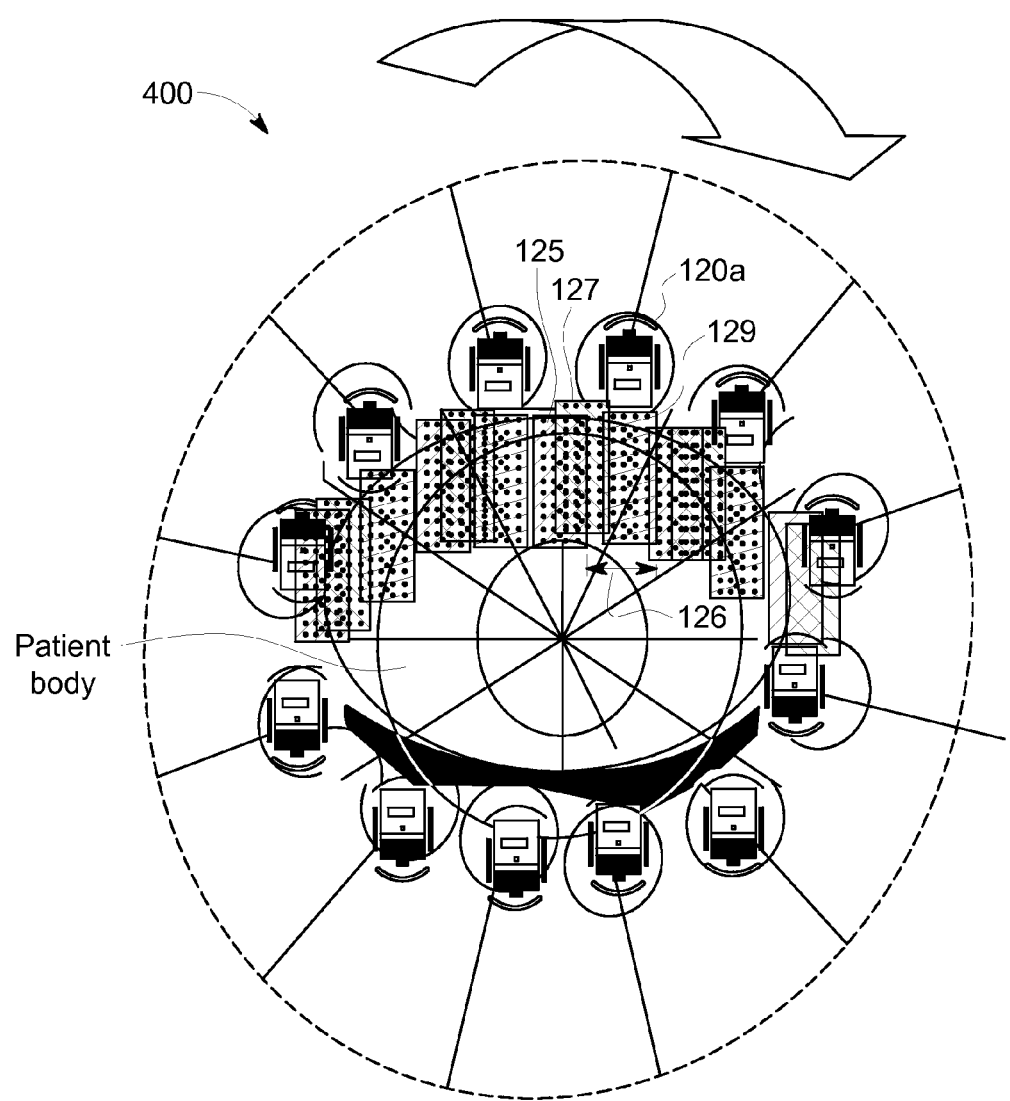
FIG. 4 is a schematic view of the gantry and detectors of the imaging system of FIG. 1 at a third rotational position.

FIG. 4 illustrates the detectors 120 at a third rotational position 400. The detectors 120 have been rotated clockwise relative to the second rotational position 300 shown in FIG. 3. For the detector 120a, for example, the in-plane FOV 129 at the third rotational position 400 is disposed generally to the right of (but still overlapping at least slightly) the in-plane FOV 127 corresponding to the second rotational position 300. As seen in FIG. 4, for the illustrated embodiment, the FOV 129 fills the remainder of the corresponding gap 126, so that additional rotational steps may not be needed to complete the particular corresponding gap. When all gaps for all detectors are covered by FOV's for the various steps (or at least all gaps disposed above a patient or with the patient within a field of view), additional rotational steps are not required. The first rotational step 200, second rotational step 300, and third rotational step 400 may be understood as providing rotation over a full imaging range, as the first rotational step 200, second rotational step 300, and third rotational step 400 provide sufficient rotation to cover the gaps between the detectors (e.g., the gaps between the in-plane FOV's in the first rotational position). The first rotational position 200 and third rotational positon 400 provide examples of end rotational positions, and the second rotational position 300 provides an example of an intermediate rotational position.

The particular order in which rotational and/or axial steps are taken and/or interleaved may vary in different embodiments. For example, in one example, the gantry 110 may be rotated over the steps of a full imaging range while at a first axial position (e.g., axial position 133 in FIG. 1). Then, the gantry and detectors may be advanced to a second axial position (e.g., axial position 135 in FIG. 1), for example by moving the bed 130 axially relative to the gantry 110. At the second axial position, the gantry may then be rotated over the steps of a full imaging range in a reverse direction to that performed at the first axial position. For example, if the gantry is rotated clockwise at the first axial position, the gantry may be rotated counterclockwise at the second axial position, for example to avoid having to return the detectors to the first rotational position before starting imaging at the second axial position. An example of the locations of the detectors for each imaging step in the first series of an iterative process, with reference to the axial positions described in connection with FIG. 1 and the rotational positions described in connection with FIGS. 2-4, is shown below. Additional steps may be provided or iteratively repeated as desired to provide a desired amount or duration of time of imaging information.

| Step | Rotational Position | Axial Position |
|---|---|---|
| 1 | 200 | 133 |
| 2 | 300 | 133 |
| 3 | 400 | 133 |
| 4 | 400 | 135 |
| 5 | 300 | 135 |
| 6 | 200 | 135 |
| 7 | 200 | 133 |
| 8 | 300 | 133 |
| ... | | |

In some embodiments, the gantry may be rotated over less than a full imaging range before adjusting axial position. An example of the locations of the detectors for each imaging step in the first series in an iterative process for which less than a full imaging range is covered before adjusting axial position is shown in the table below, with continued reference to the axial positions described in connection with FIG. 1 and the rotational positions described in connection with FIGS. 2-4 is shown below. Again, additional steps may be performed as desired to provide a desired amount or duration of time of imaging information.

| Step | Rotational Position | Axial Position |
|---|---|---|
| 1 | 200 | 133 |
| 2 | 200 | 135 |
| 3 | 300 | 135 |
| 4 | 300 | 133 |
| 5 | 400 | 133 |
| 6 | 400 | 135 |
| 7 | 200 | 135 |
| 8 | 200 | 133 |
| ... | | |

It should be noted that the above examples are provided for illustrative purposes, and that other arrangements of steps may be employed in various embodiments. For example, in some embodiments, additional and/or smaller steps may be employed. For instance, in some embodiments, intermediate axial positions may be provided between first and second axial positions.

Figure 5:
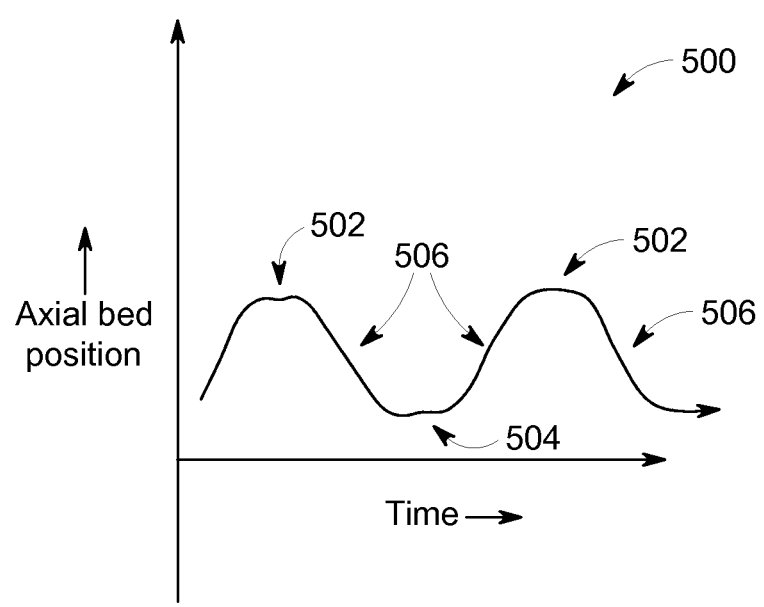
FIG. 5 is a graph corresponding to a sinusoidal movement of a bed relative to a gantry in accordance with various embodiments.

Further still, it may be noted that the motion in the rotational and/or axial directions may be generally continuous in various embodiments. FIG. 5 illustrates a curve 500 that plots bed position (e.g., along an axis of the bore of a gantry) against time. In the example of FIG. 5, the bed is advanced in a generally continuous fashion during acquisition (e.g., in continuous motion between endpoints). The curve 500 is generally sinusoidal in the illustrated embodiment, but other motions may be employed in alternate embodiments. As seen in FIG. 5, the slope of the curve 500 is substantially smaller proximate transition points 502, 504 corresponding to changes in direction. Thus, the movement of the bed may be slower at ends where the bed switches from one direction to the other to provide less or no jarring to a patient during changes in direction, while providing faster movement over the middle portion 506 of the range of motion to reduce time of travel when not as discomforting to patient. The particular speeds of the bed and configuration of the curve 500 may be tailored to a given application to provide desired levels of patient comfort as well as to reduce or minimize blurring of images acquired during motion of the bed (e.g., by reducing speed at end points of travel and/or during acquisition). Thus, in some embodiments, the gantry may be actuated in a step and shoot fashion with the bed and gantry stationary during image acquisition, while in other embodiments, actuation in at least one direction (e.g., axial) may be generally continuous during acquisition.

As discussed above in connection with FIG. 2-4, planar imaging acquisition may be performed in accordance with various embodiments. Additionally or alternatively, three-dimensional (e.g., SPECT) acquisition may be performed in some embodiments. For example, the detectors 120 may be pivoted or rotated relative to each other to sweep over a range. The additional view angles for the detectors may be used to provide three-dimensional imaging capabilities.

In some embodiments, the processing unit 140 may be configured to control the detectors to sweep over a first smaller range to collect additional information for the first smaller range relative to a second larger range, thereby acquiring sufficient information for providing a higher quality image for a region of interest positioned in the first smaller range, while reducing the overall time required for an imaging scan and/or making the most efficient use of a limited acquisition time for imaging an organ of interest.

Figure 6:
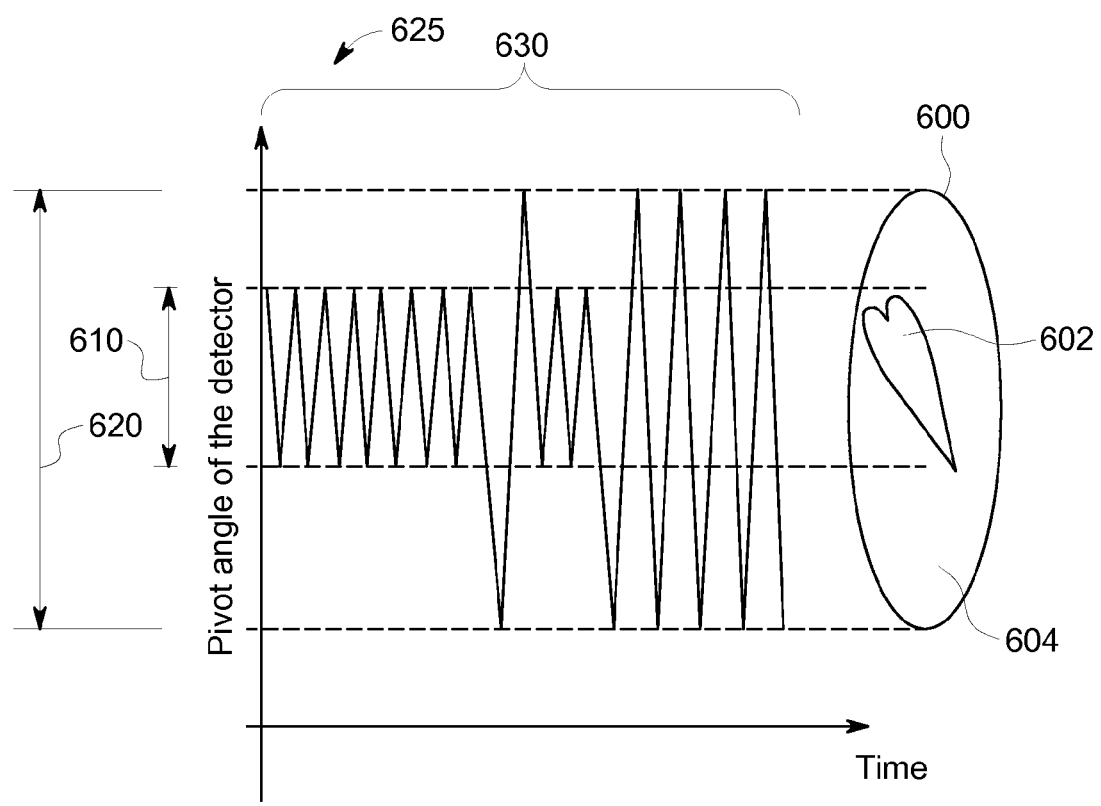
FIG. 6 depicts varying coverage of portions of a FOV in accordance with various embodiments.

For example, FIG. 6 depicts varying coverage of sweep ranges of a detector over the duration of an imaging scan. In FIG. 6 an object 600 includes an organ of interest 602 (e.g., a heart) and a supplemental volume 604 (e.g., portions of the object other than the heart that may provide useful background or comparison information). The pivot angle of a detector (e.g., detector 120) is selectively controlled to pivot over a first pivoting range 610 that provides coverage of the organ of interest 602, and over a second pivoting range 620 that provides coverage of the organ of interest 602 as well as the supplemental volume 604. As seen in FIG. 6, a larger proportion of the acquisition time is spent pivoting the detector over the first pivoting range 610 than over the second pivoting range 620. Further, the time spent on the first pivoting range 610 may be biased toward the beginning 625 of the acquisition duration 630, so that more information regarding the organ of interest 602 may be acquired during a time period of greater informational value or relatively quickly varying time period for which imaging information of the organ of interest 602 is particularly desired (e.g., during an uptake or washout phase), with imaging information for the supplemental volume 604 acquired at a less valuable or more slowly varying time period.

Figure 7:
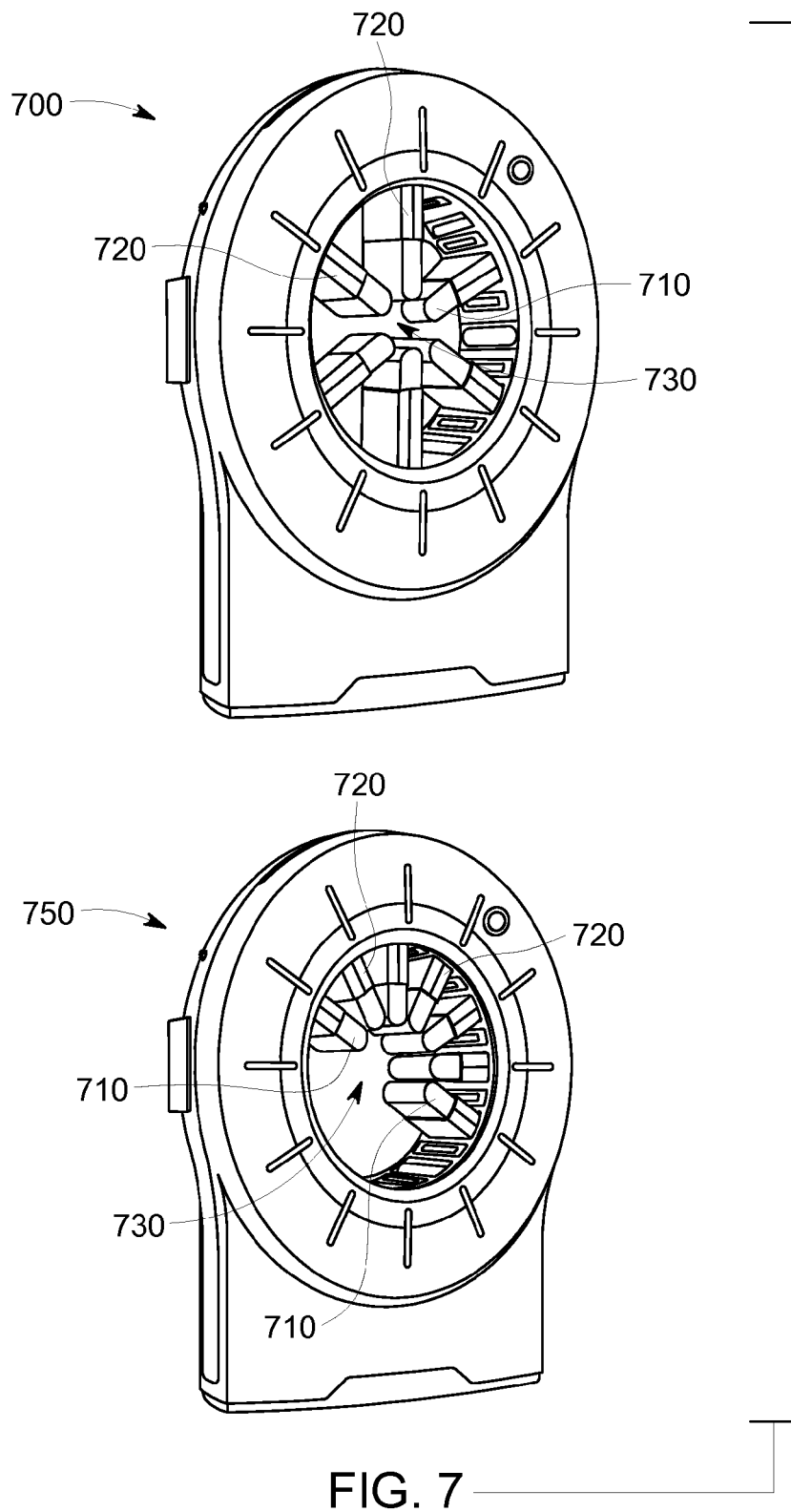
FIG. 7 is a perspective view of imaging systems in accordance with various embodiments.

FIG. 7 illustrates a first imaging system 700 and a second imaging system 750 that includes detectors 710 mounted on arms 720 about a bore 730. The first imaging system 700 includes arms 720 distributed generally uniformly about the bore 730, while the second imaging system 750 includes arms 720 disposed only about a portion of the bore 730. In FIG. 7, the detectors 710 are disposed on arms 720 that extend radially across the bore 730. It may be noted that other arrangements of arms and detectors may be employed. For example, the arms may be arranged in a generally horizontal and/or vertical direction relative to the bore 730 (see, e.g., FIG. 10).

Figure 8:
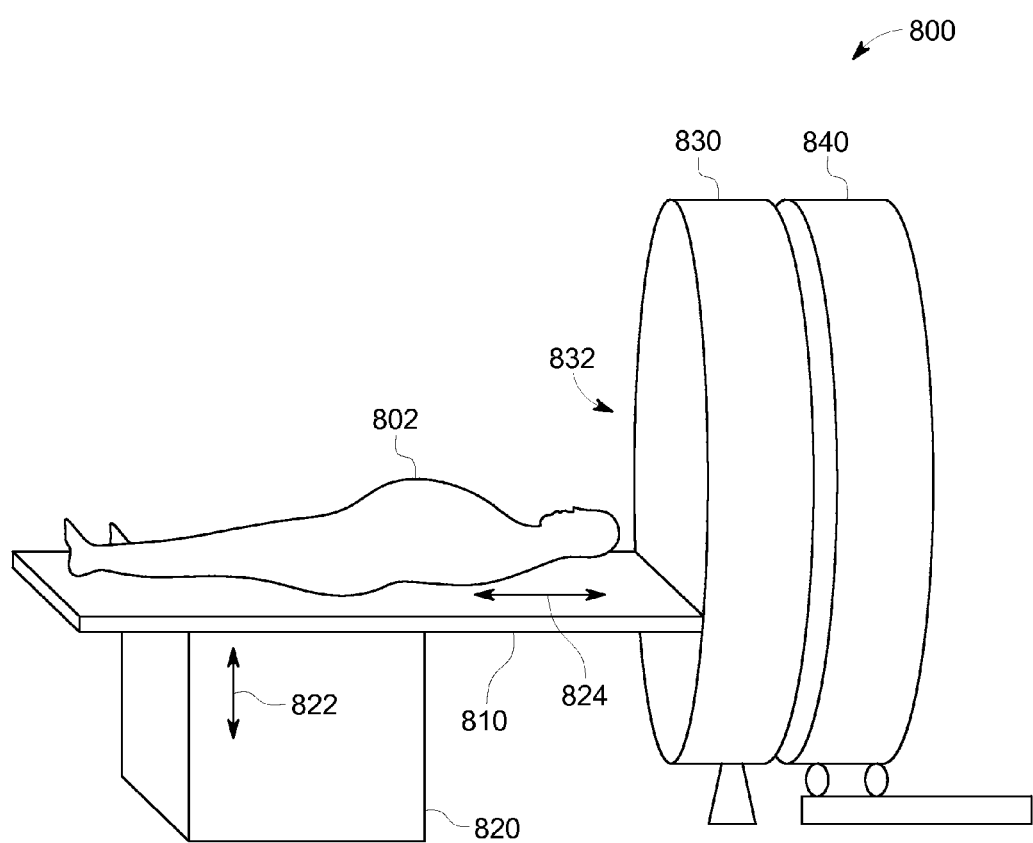
FIG. 8 is a schematic view of an imaging system with two gantries in accordance with various embodiments.

In some embodiments, NM imaging information may be acquired at two distinct axial FOV's simultaneously, alternatively or in addition to in a temporally interleaved fashion as discussed above. FIG. 8 illustrates an imaging system 800 configured to acquire simultaneous NM imaging information for two axial FOV's. The imaging system 800 includes a bed 810 on which a patient 802 to be imaged is supported. The bed 810 is coupled to an actuating mechanism 820 that articulates the bed vertically along direction 822 and horizontally (or axially into and out of the bore) along direction 824. The imaging system also includes a fixed gantry 830 and a movable gantry 840. The fixed gantry 830 and movable gantry 840 share an aligned bore 832. Each gantry includes detectors (e.g., detectors 120) not shown in FIG. 8 that may rotate with the gantry and be used to collect NM imaging information. The fixed gantry 830 may be referred to as fixed because the fixed gantry 830 is mounted to a floor or other support structure and is not axially adjustable (e.g., along direction 824), while the movable gantry 840 is adjustable axially. Thus, the bed 810 and movable gantry 840 may be axially adjusted relative to the fixed gantry 830, and relative to each other. It may be noted that, in some embodiments, the detectors of one or more of the gantries may be configured as a multiple-pinhole based camera or other configuration that need not necessarily rotate with a gantry or other support structure (e.g., the gantry or other support structure may not rotate during imaging, with only the bed articulated along an axial direction during acquisition of imaging information).

To image multiple axial FOV's simultaneously, the bed 810 may be advanced into the bore 832 until a first ROI is disposed within the fixed gantry 830. Then, the movable gantry 840 may be adjusted until a second ROI of the patient 802 is disposed within the movable gantry 840. Thus, information for two ROI's or FOV's spaced apart from each axially may be simultaneously acquired by operating the detectors of the fixed gantry 830 and the detectors of the movable gantry 840 to acquire NM imaging information with the gantries positioned about the different ROI's.

Figure 9:
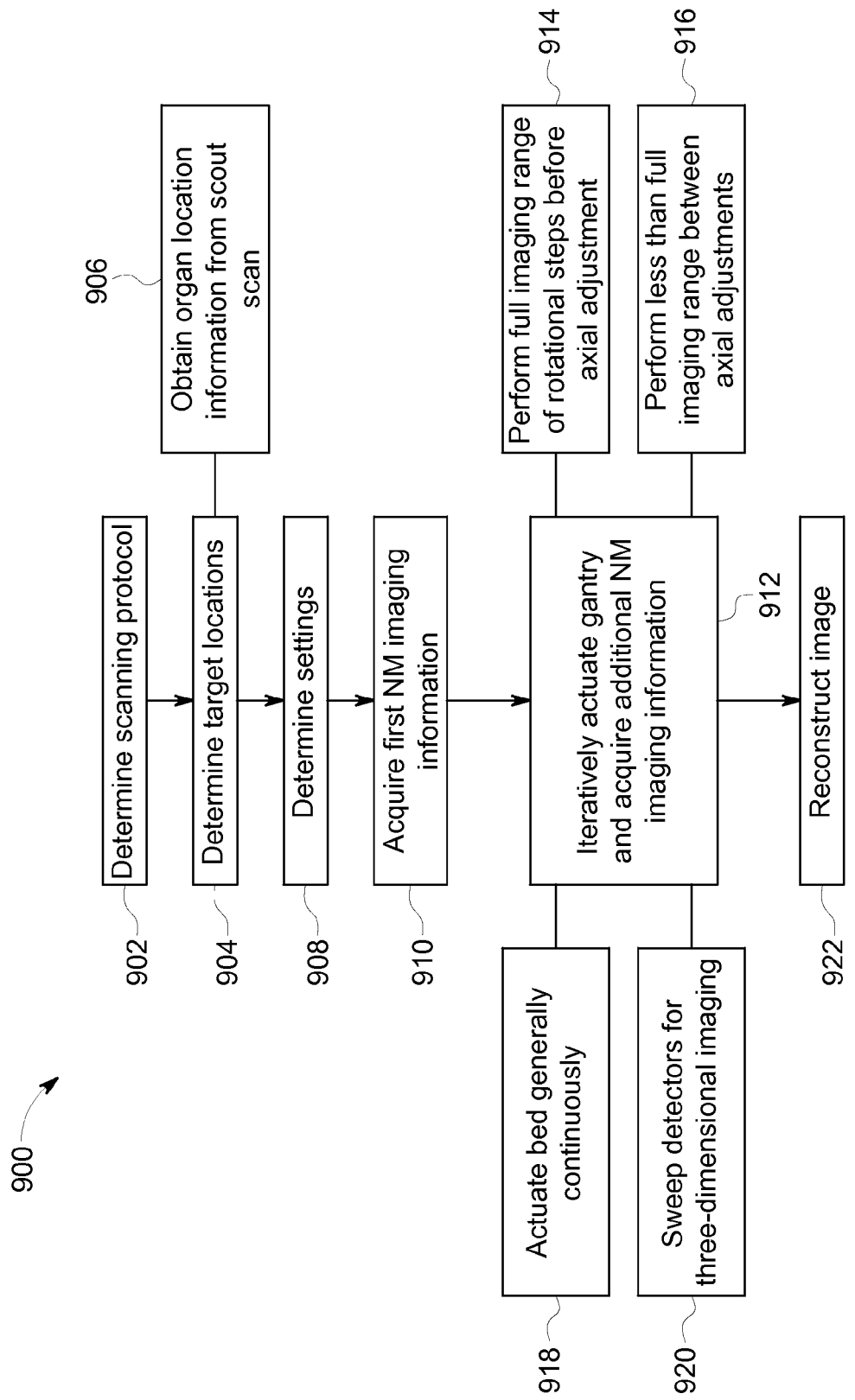
FIG. 9 is a flowchart of a method in accordance with various embodiments.

FIG. 9 provides a flowchart of a method 900 for imaging (e.g., dynamically imaging). The method 900, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 900 may be able to be used as one or more algorithms to direct hardware to perform one or more operations described herein.

At 902, a scanning protocol is determined. For example, the scanning protocol may be determined based on information provided by a user via an input unit (e.g., input unit 160).

At 904, the location of one or more target organs is determined. For example, for a dynamic renal study, the kidneys and bladder may be identified as the target organs. The target organs may be identified directly by a user input, and/or determined based on user input. The location of the target organs may be determined using imaging information, such as SPECT imaging information and/or CT imaging information. For example, in some embodiments, a scout image may be used to determine organ location. In the illustrated embodiment, at 906, organ location information is obtained from a CT acquisition unit, for example by performing a scout scan. The location of the organs of interest may be determined using computer software configured to identify organs from scout images, or may be identified by a user (e.g., via an input to a touch screen displaying a scout image).

At 908, settings for the performance of imaging acquisition are set. The settings may be based, for example, on the protocol selected or determined at 902 as well as the location of the one or more target organs determined at 904. The settings may specify, for example, various rotational and axial positions to be employed during the scan, as well as the time to be spent at each position, the order in which the positions are to be used to acquire imaging information or the like. Generally, an imaging system may be controlled pursuant to the settings to collect information for plural FOV's in a temporally interleaved fashion so that information for each FOV is collected during at least a portion of a shared time duration. For example, if a period of interest has a duration of about 20 seconds, information from each FOV may be collected during a portion of the about 20 seconds, providing for improved consistency between the images for each FOV and improved diagnostic value in comparisons between the FOV's relative to studies where images for different FOV's are acquired at separate, non-overlapping times.

At 910, first NM imaging information is acquired of an object to be imaged at a first end rotational position and a first axial position of an imaging system (e.g., imaging system 100). The first NM imaging information may be acquired, for example, shortly after introduction of a radiopharmaceutical for NM imaging is introduced into a patient to be imaged. It may be noted that an "end rotational" position may be understood as being an end position in that it corresponds to a beginning or an end of a cycle of movement between positions, and need not necessarily be physically disposed at an end of a range of motion. For example, in some embodiments, a first end rotational position, at which first NM imaging information is obtained, may be disposed at a middle or other intermediate physical position with respect to a range of rotation.

At 912, a gantry of the imaging system is actuated iteratively in a series of steps between the first end rotational position and a second end rotational position as well as between the first axial position and a second axial position. Additional NM imaging information may be acquired at each step. The axial positions may correspond to different FOV's along an axis of the object (the FOV's may be adjacent, overlapping, or spaced apart), and the rotational positions may be configured to provide a full imaging range (e.g., to account for any gaps between in-plane FOV's of detectors). As discussed herein, for example, at least some of the actuations (e.g., motion of a bed axially) may be performed in a generally continuous fashion (e.g., to reduce patient discomfort caused by repeated starting and stopping of a bed (at 918). Further in some embodiments, a full imaging range of rotational steps may be acquired before adjusting an axial position (at 914), while in other embodiments less than a full imaging range of rotational steps may be acquired between axial adjustments (at 916). In some embodiments, detectors may be maintained aligned or parallel to obtain planar NM imaging information. Additionally or alternatively, in some embodiments, detectors may be pivoted with respect to each other or swept for some or all acquisition steps to provide three-dimensional imaging information (at 920). For example, detectors may be swept over a first pivoting range corresponding to an organ of interest for more time than over a second pivoting range corresponding to a supplement volume during an imaging or scanning process.

At 922, an image is reconstructed using the information acquired at 910 and 912. It may be noted that the "image" need not necessarily be limited to a single printed or otherwise displayed page or screen. The image for example, may be dynamically presented to a viewer (e.g., via display unit 170) during the acquisition process. The information from 910 and 912 used to reconstruct or present the image may be understood as being collected during a single, generally continuous acquisition or scanning process. For example, the information acquired for two or more axial FOV's may be acquired in a temporally interleaved fashion as discussed herein, in contrast to separate imaging process performed at distinct and non-overlapping time frames for two or more FOV's.

Figure 10:
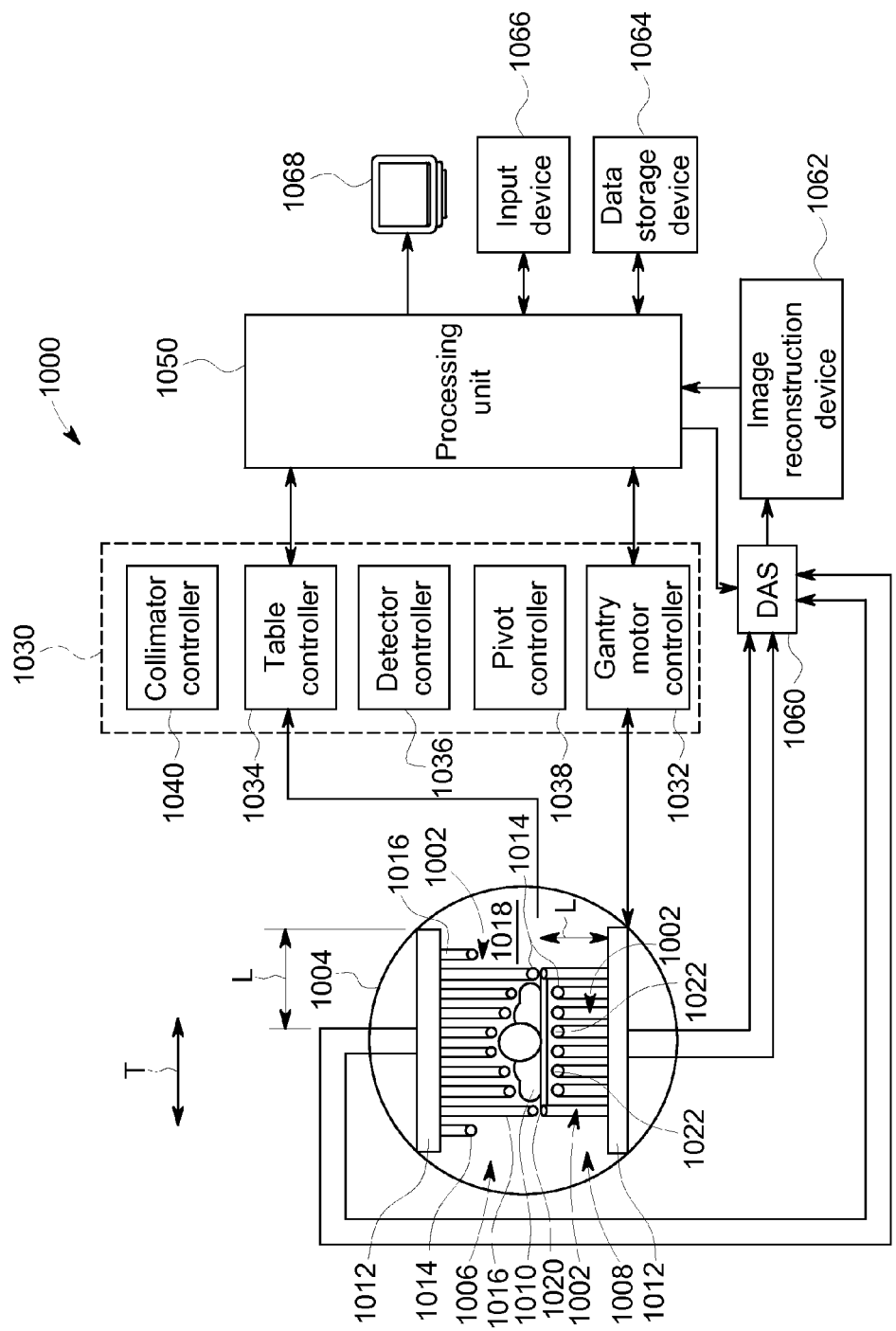
FIG. 10 is a schematic block diagram of a Nuclear Medicine (NM) imaging system in accordance with an embodiment.

Various methods and/or systems (and/or aspects thereof) described herein may be implemented using a medical imaging system. For example, FIG. 10 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). In particular, a plurality of imaging detectors 1002 are mounted to a gantry 1004. Each detector 1002 may include, for example, collimators and detectors arranged generally similarly to the arrangements discussed in connection with FIGS. 1-9. In the illustrated embodiment, the imaging detectors 1002 are configured as two separate detector arrays 1006 and 1008 coupled to the gantry 1004 above and below a subject 1010 (e.g., a patient), as viewed in FIG. 10. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 10). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels. In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 10 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially as described in more detail herein.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually as described in more detail herein. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022, as shown for example in FIG. 3, or as shown by detector 410 in FIG. 4, as another example. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 10 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
    a gantry having a bore therethrough;
    a bed that is translatable between a first axial position and a second axial position along an axis of the bore of the rotating gantry, the bed configured to support an object to be imaged, the first axial position having a first field of view corresponding to a first portion of the object, the second axial position having a second field of view corresponding to a second portion of the object that is different from the first portion;
    plural nuclear medicine (NM) imaging detectors disposed about the bore of the gantry, the NM imaging detectors having an axial field of view; and
    a processing unit operably coupled to the imaging detectors, the processing unit configured to:
        acquire first NM imaging information of the object from the imaging detectors with the imaging detectors in the first axial position;
        iteratively actuate the gantry in a series of steps back and forth between the first axial position and the second axial position, wherein the series of steps comprises plural steps at each of the first and second axial positions;
        acquire additional NM imaging information of the object at each of the steps; and
        reconstruct an image of the object using the first NM imaging information and the additional NM imaging information, wherein the image corresponds to an axial field of view that is larger than the axial field of view of the imaging detectors.

2. The imaging system of claim 1, wherein the gantry is a rotating gantry, wherein the NM imaging detectors have an in-plane field of view, the imaging detectors having corresponding gaps therebetween wherein an in-plane field of view of each detector does not overlap with corresponding in-plane fields of views of at least one immediately adjacent imaging detector, and wherein the processing unit is configured to:
    acquire the first NM imaging information of the object from the imaging detectors with the imaging detectors in a first end rotational position and the first axial position; and
    iteratively actuate the gantry in a series of steps between the first end rotational position and a second end rotational position, and between the first axial position and the second axial position.

3. The imaging system of claim 2, wherein the processing unit is configured to rotate the gantry over a full imaging range in a first direction from the first end rotational position to the second end rotational position while the imaging detectors remain at the first axial position, then advance the imaging detectors to the second axial position, and then rotate the gantry over the full imaging range in a second direction opposite to the first direction from the second end rotational position to the first end rotational position with the detectors at the second axial position, wherein rotating the gantry over the full imaging range corresponds to a rotation of the gantry sufficient to provide imaging information over the gaps between the in-plane fields of view of the imaging detectors.

4. The imaging system of claim 2, wherein the processing unit is configured to rotate the gantry over less than a full imaging range before adjusting an axial position, wherein rotating the gantry over the full imaging range corresponds to a rotation of the gantry sufficient to provide imaging information over the gaps between the in-plane fields of view of the imaging detectors.

5. The imaging system of claim 1, wherein the processing unit is configured to axially oscillate the bed generally continuously over a duration of an imaging scan.

6. The imaging system of claim 5, wherein the processing unit is configured to oscillate the bed sinusoidally with respect to time during the duration of the imaging scan.

7. The imaging system of claim 1, wherein the processing unit is configured to align the imaging detectors parallel with respect each other during rotation, and wherein the image reconstructed is a planar image.

8. The imaging system of claim 1, wherein the processing unit is configured to rotate the imaging detectors relative to each other, and wherein the image reconstructed is a three-dimensional image.

9. The imaging system of claim 8, wherein a first pivoting range of the detectors corresponds to an organ of interest and a second pivoting range corresponds to a supplemental volume, wherein the processing unit is configured to sweep the detectors over the first pivoting range for a longer duration of time than over the second pivoting range during performance of an imaging scan.

10. The imaging system of claim 1, further comprising a computed tomography (CT) detector, wherein the processing unit is configured to obtain organ location information from the CT detector, and to determine the first and second axial positions based on the organ location information.

11. The method of claim 10 further comprising obtaining organ location information from a computed tomography (CT) detector, and determining the first and second axial positions based on the organ location information.

12. A method comprising:
acquiring first nuclear medicine (NM) imaging information of an object to be imaged with plural NM imaging detectors at a first axial position, the imaging detectors disposed about a gantry having a bore therethrough, with the object disposed on a bed translatable along an axis of the bore between the first axial position and a second axial position, the imaging detectors having an axial field of view, the first axial position defining a first field of view corresponding to a first portion of the object, the second axial position defining a second field of view corresponding to a second portion of the object that is different from the first portion;
iteratively actuating the gantry in a series of steps back and forth between the first axial position and the second axial position, wherein the series of steps comprises plural steps at each of the first and second axial positions;
acquiring additional NM imaging information of the object at each of the steps; and
reconstructing an image of the object using the first NM imaging information and the additional NM imaging information, wherein the image corresponds to an axial field of view that is larger than the axial field of view of the imaging detectors.

13. The method of claim 12, wherein the first NM imaging information is acquired at the first axial position and a first end rotational position, wherein the imaging detectors have an in-plane field of view, the imaging detectors having corresponding gaps therebetween wherein an in-plane field of view of each detectors does not overlap with corresponding in-plane fields of views of at least one immediately adjacent imaging detector, and wherein iteratively actuating the gantry comprises iteratively actuating the gantry in a series of steps between the first end rotational position and a second end rotational position, and between the first axial position and the second axial position.

14. The method of claim 13, wherein iteratively actuating the gantry comprises:
rotating the gantry over a full imaging range in a first direction from the first end rotational position to the second end rotational position while the imaging detectors remain at the first axial position, wherein rotating the gantry over the full imaging range corresponds to a rotation of the gantry sufficient to provide imaging information over the gaps between the in-plane fields of view of the imaging detectors;
then advancing the imaging detectors to the second axial position;
then rotating the gantry over the full imaging range in a second direction opposite to the first direction from the second end rotational position to the first end rotational position with the detectors at the second axial position.

15. The method of claim 13, wherein iteratively actuating the gantry comprises rotating the gantry over less than a full imaging range before adjusting an axial position, wherein rotating the gantry over the full imaging range corresponds to a rotation of the gantry sufficient to provide imaging information over the gaps between the in-plane fields of view of the imaging detectors.

16. The method of claim 12, wherein iteratively actuating the gantry comprises axially oscillating the bed with respect to the bore of the gantry generally continuously over a duration of an imaging scan.

17. The method of claim 16, comprising oscillating the bed sinusoidally with respect to time during the duration of the imaging scan.

18. The method of claim 17, further comprising rotating the detectors over a first pivoting range corresponding to an organ of interest and a second pivoting range corresponding to a supplemental volume, wherein the detectors are swept over the first pivoting range for a longer duration of time than over the second pivoting range during performance of an imaging scan.

19. The method of claim 12, wherein the first axial position corresponds to a kidney and the second axial position corresponds to a bladder, further comprising performing a dynamic renal study using the first NM imaging information and the additional NM imaging information.

20. An imaging system including:
a first gantry having a bore therethrough;
a second gantry axially aligned with the first rotating gantry and configured to be translatable axially relative to the first rotating gantry;
a bed that is translatable along an axis of the bore of the first gantry;
plural nuclear medicine (NM) imaging detectors disposed about the bore of the first gantry and the second gantry, the imaging detectors having an axial field of view; and
a processing unit operably coupled to the imaging detectors, the processing unit configured to:
axially translate the bed and the second gantry with respect to the first gantry to position the first gantry about a first region of interest and to position the second gantry about a second region of interest;
acquire, concurrently, NM imaging information from the imaging detectors of the first region of interest and the second region of interest; and
reconstruct an image using the NM imaging information.

* * * * *